(12) United States Patent
Lou et al.

(10) Patent No.: US 6,368,633 B1
(45) Date of Patent: Apr. 9, 2002

(54) MICROPARTICLES WHICH CONTROLLABLY RELEASE OLFACTORILY ACTIVE SUBSTANCES, METHODS OF USING SAME AND PROCESSES FOR PREPARING SAME

(75) Inventors: Wen Chin Lou, Morris Plains; Keith J. McDermott, Bridgewater; Shmuel David Shefer; Adi Shefer, both of East Brunswick; John M. Teffenhart, Edison; Chee-Teck Tan, Middletown; Jerome I. Lindauer, Hillsdale; Leslie C. Smith, Princeton, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/854,707

(22) Filed: May 14, 2001

Related U.S. Application Data (62) Division of application No. 09/468,135, filed on Dec. 21, 1999, now Pat. No. 6,235,274.

(51) Int. Cl.[7] .............................. A61K 9/14; A61K 9/68; A61K 7/16; A61K 9/48; A61K 9/50

(52) U.S. Cl. ........................ 424/489; 424/48; 424/49; 424/451; 424/457; 424/458; 424/461; 424/493; 424/499; 426/5; 512/1; 512/3; 512/4

(58) Field of Search ................................ 424/451, 457, 424/458, 461, 489, 493, 499, 48, 49; 512/1, 4, 3; 426/5

(56) References Cited

U.S. PATENT DOCUMENTS

| | | | | |
|---|---|---|---|---|
| 3,314,803 A | | 4/1967 | Dame et al. | |
| 4,556,565 A | * | 12/1985 | Arima et al. | 426/3 |
| 5,198,251 A | * | 3/1993 | Song et al. | 426/5 |
| 5,356,615 A | * | 10/1994 | Gaffar | 424/49 |
| 5,370,881 A | * | 12/1994 | Fuisz | 426/5 |
| 5,603,971 A | | 2/1997 | Porzio, I et al. | |
| 5,897,897 A | | 4/1999 | Porzio, II et al. | |

FOREIGN PATENT DOCUMENTS

JP 04218583 A * 8/1992

* cited by examiner

*Primary Examiner*—Jose' G. Dees
*Assistant Examiner*—Marina Lamm
(74) *Attorney, Agent, or Firm*—Joseph F. Leightner (57) ABSTRACT

Described are flavor composition, flavor component, perfume composition and perfume component-containing microparticles which are particulate matrices composed of:

(a) an olfactorily active component (e.g., perfume component);

(b) silica; and (c) a saccharide composition which is a mixture of mannitol and maltose.

The microparticles are useful in augmenting, enhancing and/or imparting aroma and/or taste (over relatively long periods of time in a controllably releasable manner) to perfume compositions, perfumed articles (e.g., deodorancy and antiperspirant sticks), foodstuffs, chewing gums, beverages and the like. Also described is a process for preparing the above-mentioned microparticles using, in sequence, (1) adsorption of the olfactorily active material onto silica followed by (2) a blending/extrusion step followed by (3) at least one particularization step.

7 Claims, 7 Drawing Sheets

MICROPARTICLES WHICH CONTROLLABLY RELEASE OLFACTORILY ACTIVE SUBSTANCES, METHODS OF USING SAME AND PROCESSES FOR PREPARING SAME

This is a Divisional of prior application Ser. No.:09/468,135, filed Dec. 21, 1999 now U.S. Pat. No. 6,235,274.

BACKGROUND OF THE INVENTION

Our invention relates to olfactorily active component-containing microparticles which are useful in augmenting, enhancing and/or imparting aroma and/or taste (over relatively long periods of time in a controllably releasable manner) to perfume compositions, perfumed articles, foodstuffs, chewing gums, beverages and the like.

A particular need exists for deodorant and antiperspirant compositions having pleasant fragrances which last for a relatively long period of time on use. Furthermore, a particular need exists for chewing gums, for example, having a pleasant flavor which lasts for a relatively long period of time.

It is known in the prior art to produce compositions for contacting the skin wherein a fragrance is released from the composition after application of the composition to the skin, that is, body activated fragrances. It is desired that such products produce a low level of odor prior to application to the skin, but which release fragrance over a long period of time after application to the skin.

It is also known in the art to control human body odors by use of deodorant products, particularly in the underarm area of the body. Deodorant products generally contain a perfume or other odor masking ingredients in a vehicle from which active ingredients may be deposited on the skin. The deodorant products may be in the form of solid or semisolid sticks.

Furthermore, it is known to delay release of the fragrance from a composition by methods such as microencapsulation of the fragrance substance. By the same token, it is known to delay release of flavors from the composition by methods such as microencapsulation of the flavor substance.

However, a delayed fragrance release from a deodorant stick has not effectively been obtained using microencapsulation principally because microencapsulating a fragrance in a water-containing deodorant stick base dissolves the protective microencapsulation coating and prematurely releases the fragrance. Indeed, several attempts at attaning fragrance longevity for such antiperspirant and deodorant products have been made in the art employing encapsulation and spray drying techniques. Prior methods have produced inconsistent results, either because they have involved a rupturing of microcapsule walls by mechanical pressure to achieve fragrance release or encapsulating polymers have generally presented incompatibility problems with the fragrance resulting in distortion of the fragrance profile.

By the same token, a delayed flavor evolution from a chewing gum stick has not been effectively obtained using microencapsulation, principally because microencapsulating a flavor in a chewing gum stick activated by water dissolves the protective microencapsulation coating and prematurely releases the flavor, so that after several minutes of chewing, no flavor remains. Indeed, several attempts at attaining flavor longevity for such chewing gum products and the like have been made in the art employing encapsulation and spray drying techniques. Prior methods have produced inconsistent results, either because they have involved a rupturing of microcapsule walls by mechanical pressure to achieve flavor release or encapsulating polymers have generally presented incompatibility problems with the flavor resulting in distortion of the flavor profile.

U.S. Pat. No. 5,614,179 teaches deodorant products containing a polymer/fragrance encapsulated by carbon and ingredient A deodorant or antiperspirant-deodorant cosmetic stick comprises an organic matrix having a dispersed particle phase of an encapsulated bicarbonate salt such as sodium bicarbonate. The particle surfaces are coated with a film forming medium comprising a blend of a polymer and a fragrance. When this product is applied to underarm surfaces, the deodorizing activity is signaled by the release of a fragrance aroma.

U.S. Pat. No. 4,731,243, which is incorporated herein by reference, teaches deodorant and/or antiperspirant sticks which contain suspended therein fragrance containing polymeric pellets containing 1 to 80% fragrance. The polymeric pellets are produced by means of cryogenically grinding an extruded mixture of perfume composition and polymer. U.S. Pat. No. 4,428,869, which is also incorporated herein by reference, teaches a microcapsule suspension of a fragrance which yields a continuously high fragrance intensity release, evenly and uniformly over an extended period of time. None of these prior disclosures achieve a fragrance release evenly over a long period of time resulting from contact with skin moisture.

Accordingly, it is still desired to provide deodorant or antiperspirant compositions having a delayed release of fragrance evenly over an extended period of time. It is particularly desired to provide such product wherein the fragrance is released after contact of the composition with skin moisture.

With respect to encapsulated flavors, U.S. Pat. No. 5,603,971 issued on Feb. 18, 1997 and U.S. Pat. No. 5,897,897 issued on Apr. 27, 1999, each disclose a flavor encapsulation composition comprising:

(a) a flavoring material encapsulated in;

(b) a glassy matrix of matrix components consisting essentially of 85 to 95 weight percent of a modified starch and 5 to 15 weight percent of a polyhydric alcohol wherein said polyhydric alcohol is selected from the group consisting of propylene glycol and glycerin and wherein the composition is prepared by a process comprising:

(i) mixing (a) said modified starch; (b) a component selected from the group consisting of polyhydric alcohol and mixtures of polyhydric alcohol with water; and (c) a flavor composition in an extruder to obtain a melted matrix; and (ii) extruding the melted matrix.

Among the flavoring agents disclosed in U.S. Pat. No. 5,897,897 and in U.S. Pat. No. 5,603,971 are natural extracts, oleoresins, essential oils, protein hydrolysates, aqueous reaction flavors and compounded flavors.

U.S. Pat. No. 3,314,803 issued on Apr. 18, 1967 entitled "MANNITOL FIXED FLAVOR AND METHOD OF MAKING SAME" discloses a process for making a dry flavor enhancer containing a stable level of acetaldehyde in an amount effective to produce flavor enhancement, which comprises forming an aqueous solution of mannitol and acetaldehyde and spray drying said solution to obtain a powder product More specifically, U.S. Pat. No. 3,314,803 discloses a process for making a dry, stable flavor enhancer containing acetaldehyde in an amount effective to produce flavor enhancement up to about 4% by weight, which comprises forming a supersaturated solution of 2–10 parts by weight of mannitol and 1–2 parts by weight of acetaldehyde in parts by weight of water; cooling said solution to below about room temperature without crystallizing the mannitol; atomizing said solution into droplets; and passing said droplets through a drying chamber whereby a powdered product is obtained.

Nothing in any of the foregoing references discloses techniques for the production of the microparticles of our invention or processes for producing same, with said microparticles having unexpected, unobvious and advantageous properties with respect to the controllable release of olfactorily active components contained in a matrix in said microparticles.

THE INVENTION

Our invention is directed to a particulate composition comprising microparticles which are capable of controllably releasing olfactorily active substances, each of which microparticle has an effective diameter of from about 10 up to about 50 microns, and each of which microparticle has a matrix of flavor composition-bearing, flavor component-bearing, perfume composition-bearing or perfume component-bearing silica particles intimately admixed with a saccharide composition consisting essentially of a mixture of maltose and mannitol.

Our invention is further directed to a process for preparing such microparticles, which controllably release one or more aroma chemicals, perfume compositions, flavor compositions or flavor components therefrom into the environment surrounding said particles, comprising the steps of:

(a) adsorbing a fragrance composition or an aroma chemical composition or a flavor composition or a flavor component onto silica powder by means of fluidized bed plating in order to provide a flavor composition-bearing, a perfume composition-bearing, a perfume component-bearing or a flavor component-bearing silica powder composition;

(b) providing a molten saccharide composition consisting essentially of a mixture of maltose and mannitol;

(c) providing an extruder having an extruder input zone and an extruder output zone and having a screw speed of 150–400 rpm;

(d) substantially simultaneously introducing (i) said saccharide composition and (ii) said flavor composition-bearing, said fragrance composition-bearing, said fragrance component-bearing or said flavor component-bearing silica composition into the extruder at the extruder input zone;

(e) effecting the blending for a residence time of 30–150 seconds at a temperature in the range of from about 90° C. up to about 140° C. of the saccharide composition with the flavor composition-bearing, fragrance composition-bearing, flavor component-bearing or fragrance component-bearing silica powder composition in the extruder on operation of the extruder, whereby a fragrance composition-bearing, fragrance component-bearing, flavor composition-bearing or flavor component-bearing silica-saccharide tow is formed in the extruder and exits from the extruder at the extruder output zone;

(f) causing the resulting tow to solidify using drum chilling; and (g) converting the resulting solidified drum-chilled tow into particles by means of the unit operation of grinding.

The resulting microparticles are useful in augmenting, enhancing and/or imparting aroma and/or taste (over relatively long periods of time in a controllably releasable manner) to perfume compositions, perfumed articles (e.g., deodorant sticks and antiperspirant sticks), food stuffs, chewing gums, beverages and the like. The microparticles produced according to our invention are particularly useful in augmenting, enhancing and/or imparting aroma and/or taste over relatively long periods of time in a controllably releasable manner to deodorant sticks, antiperspirant sticks and chewing gum.

More specifically, the maltose:mannitol blends used to produce the microparticles of our invention contain a weight ratio of maltose:mannitol of from about 10 parts mannitol:60 parts maltose down to 60 parts mannitol:10 parts maltose. In carrying out the process of our invention, a fragrance or a flavor is first adsorbed onto silica by means of "plating" using a fluidized bed plating apparatus, e.g., a NIRO AEROMATIC® fluidized bed plating apparatus. Fragrance loadings of between about 40% up to about 70% result in a dry, free flowing, pourable product. Prior to compounding the fragrance-silica resulting from the plating step with the maltose:mannitol product, the mixture of maltose and mannitol is melted, and the resulting maltose:mannitol melt is compounded with the fragrance "plated" silica in an extruder by applied heat and shear.

Any single screw or twin screw extruder may be used, but preferred, is the Werner & Phleiderer extruder.

The extrusion process for carrying out the process of our invention is based on control of two specific variables:

(i) the barrel temperature of the extruder; and (ii) the flow rate of material being processed through the extruder.

Thus, the range of extruder temperatures in the various barrel zones are from about 80° C. up to about 140° C.; the screw frequency is from about 150 rpm up to about 400 rpm; the flow rate is from about 8 up to about 20 kg per hour; the barrel pressure may vary from about 10 psig up to about 40 psig; and the average residence time of product being processed within the extruder is from about 30 seconds up to about 150 seconds.

The extrusion tow evolving from the extruder is cooled and particularized via, for example, cryogenic grinding. The cooling step ahead of the grinding step is carried out using a drum chilling unit operation according to standard drum chilling procedure well known to those having ordinary skill in the art. Thus, during the drum chilling procedure, the hot extrudate is forced between two chilled rollers to form flakes. The cooling process lasts for approximately 1–3 minutes for flakes to reach room temperature, and this results in a cooling rate of between about 40 up to about 60° C. per minute.

Preferably, the extruder is divided into six different temperature controlled barrel zones between 80° C. and 140° C.

Subsequent to the drum chilling/cooling process, the resulting product is then subjected to cryogenic grinding using liquid nitrogen as specifically set forth in U.S. Pat. No. 4,731,243, the specification for which is incorporated by reference herein.

The resulting product is then incorporated into materials which require extended release control release flavors, e.g., chewing gum, or extended release control release fragrances, e.g., deodorant or antiperspirant sticks, in accordance with the procedures and examples of, for example, U.S. Pat. No. 4,731,243, the specification for which is incorporated by reference herein.

It is to be emphasized that our invention is also directed to a process for preparing solid particles, which not only controllably release one or more perfume component compositions or perfume compositions or flavor compositions or flavor component compositions (also called "olfactory sense effecting compositions of matter"), but which also have an initial burst release and a response whereby the olfactory sense effecting compositions of matter are initially released in a relatively fast manner when exposed to water.

DETAILED DESCRIPTION OF THE DRAWINGS

Figure 1:
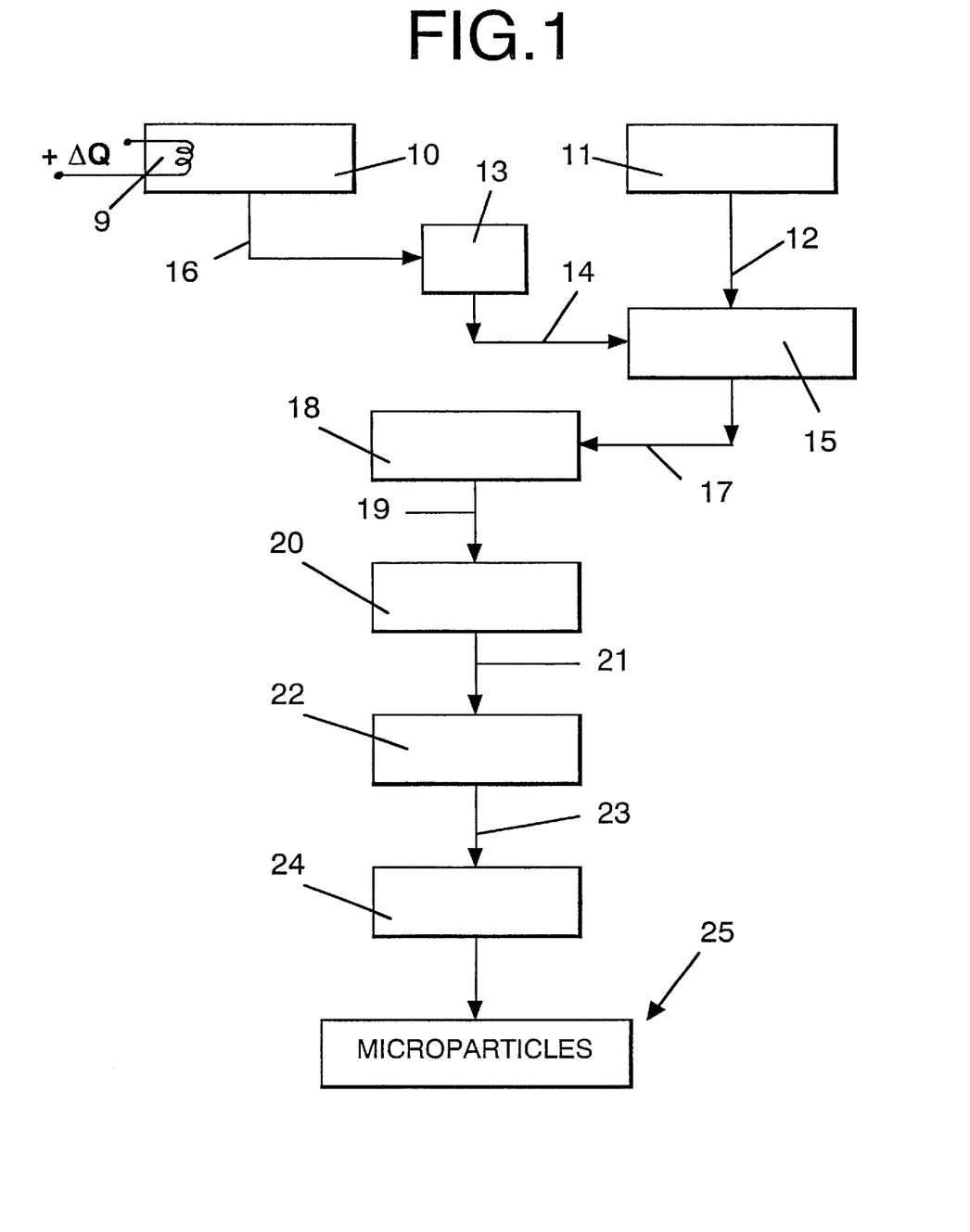
FIG. 1 is a schematic block flow diagram of the steps involved in the preparation of the solid microparticles of our invention.

Relating to the process of our invention for preparing solid particles to FIG. 1, FIG. 1 shows the process for preparing solid particles, which (i) controllably release one or more olfactory sense effecting compositions of matter therefrom into the environment surrounding said particles and (ii) provide a first release of olfactory sense effecting compositions of matter when contacted with water comprising the steps of:

(a) adsorbing an olfactory sense effecting composition of matter from location 11 onto silica via conveyance means 12, at location 15 with the silica being conveyed from source 13 via conveyance means 14;

(b) providing a molten saccharide composition consisting essentially of a mixture of maltose and mannitol from location 10 heated to the melting point using heating means 9;

(c) providing an extruder indicated by reference numeral 18 having an extruder input zone and an extruder output zone and a screw speed of 150–400 rpm;

(d) introducing (i) said saccharide composition from location 10 in the molten state via conveyance means 16 into the extruder 18, and (ii) said olfactory sense effecting composition of matter plated on silica from location 15 via conveyance means 17 into extrusion means 18 at the extruder input zone;

(e) effecting the blending for a residence time of 30–150 seconds at a temperature in the range of from about 80° C. up to about 140° C. of the saccharide composition with the olfactory sense effecting composition of matter plated on silica in the extruder 18 on operation of the extruder 18 whereby an olfactory sense effecting composition-bearing silica-saccharide tow is formed in the extruder 18 and exits from the extruder at the extruder output zone;

(f) causing the resulting tow to solidify using drum chilling means 20, the tow being conveyed from the extruder to the drum chiller via conveyance means 19; and (g) converting the resulting solidified drum-chilled tow into particles 25 by means of the unit operation of grinding via, preferably, cryogenic grinding means 22, conveyance means 23 to sieving means 24.

Figure 2:
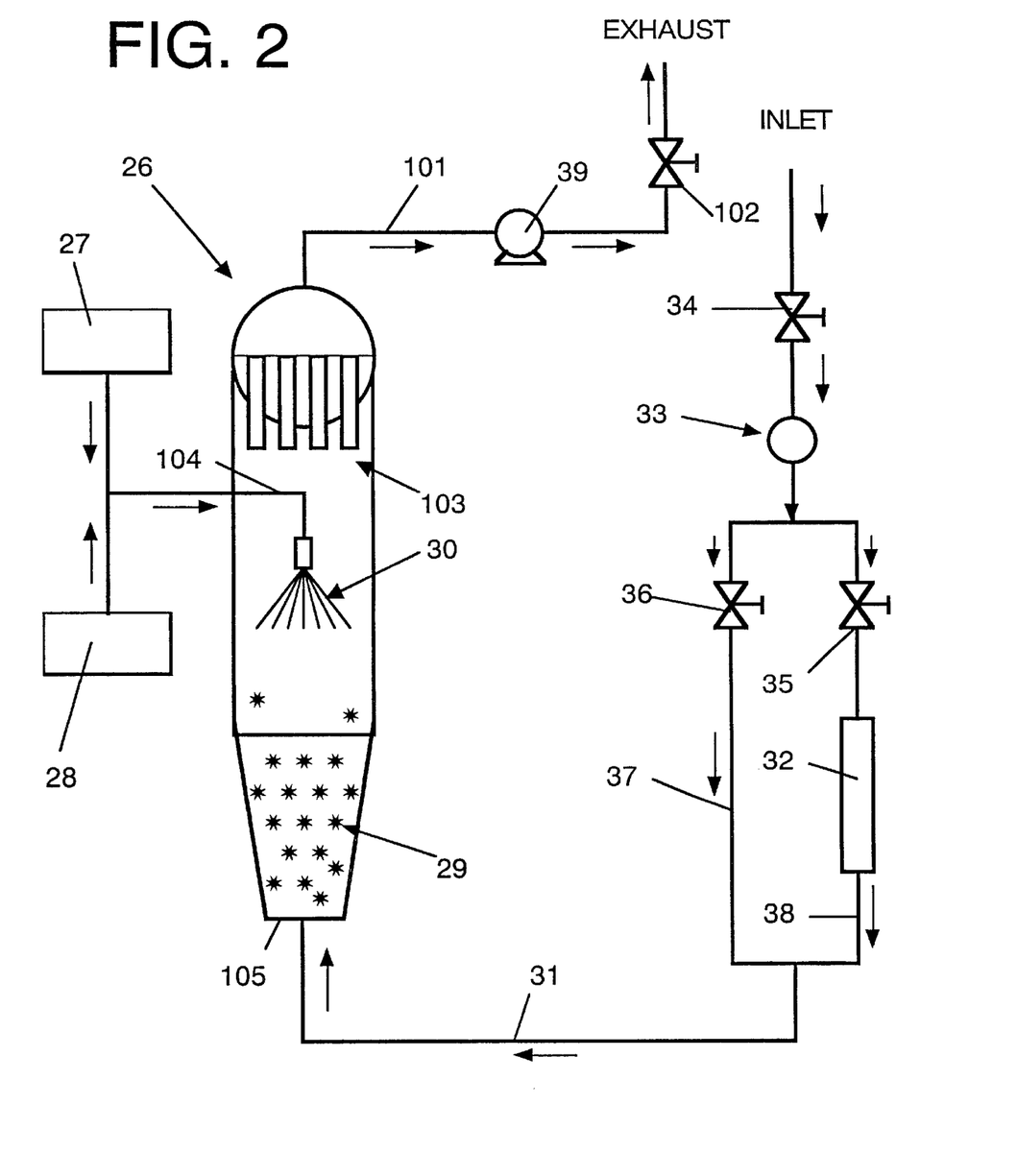
FIG. 2 is a schematic diagram indicating the process in detail for preparing the silica plated with the olfactory sense effecting substance, e.g., flavor composition, flavor composition component, perfume composition or perfume composition component. This step is indicated referring to reference numerals 11, 12, 13, 14 and 15 of FIG. 1.

Referring to FIG. 2, wherein the olfactory sense effecting composition of matter, e.g., fragrance composition, is adsorbed onto silica powder by means of fluidized bed plating, the silica powder 29 is placed in the plating apparatus indicated by reference numeral 26 factory sense effecting composition, e.g., fragrance composition or flavor composition from location 28 is admixed with atomizing air from location 27 and conveyed via line 104 downwardly (shown by reference numeral 30) onto fluidized silica 29 which is fluidized in place in an air stream emanating from line 31 through the lower part of the apparatus 105. Excess air exits from the apparatus through filters 103 and line 101 using blower 9, through valve 102. Entry air from line 31 originates through valve 34 past air chiller 33 through line 37 past valve 36 and through line 35 past heater 32 and again through line 38. Thus, the temperature of the air that is flowing into the fluid bed plating apparatus may be carefully controlled via the chiller 33 as well as the heater 32 and bypass line 37 using control valves 34, 36 and 35.

Figure 3:
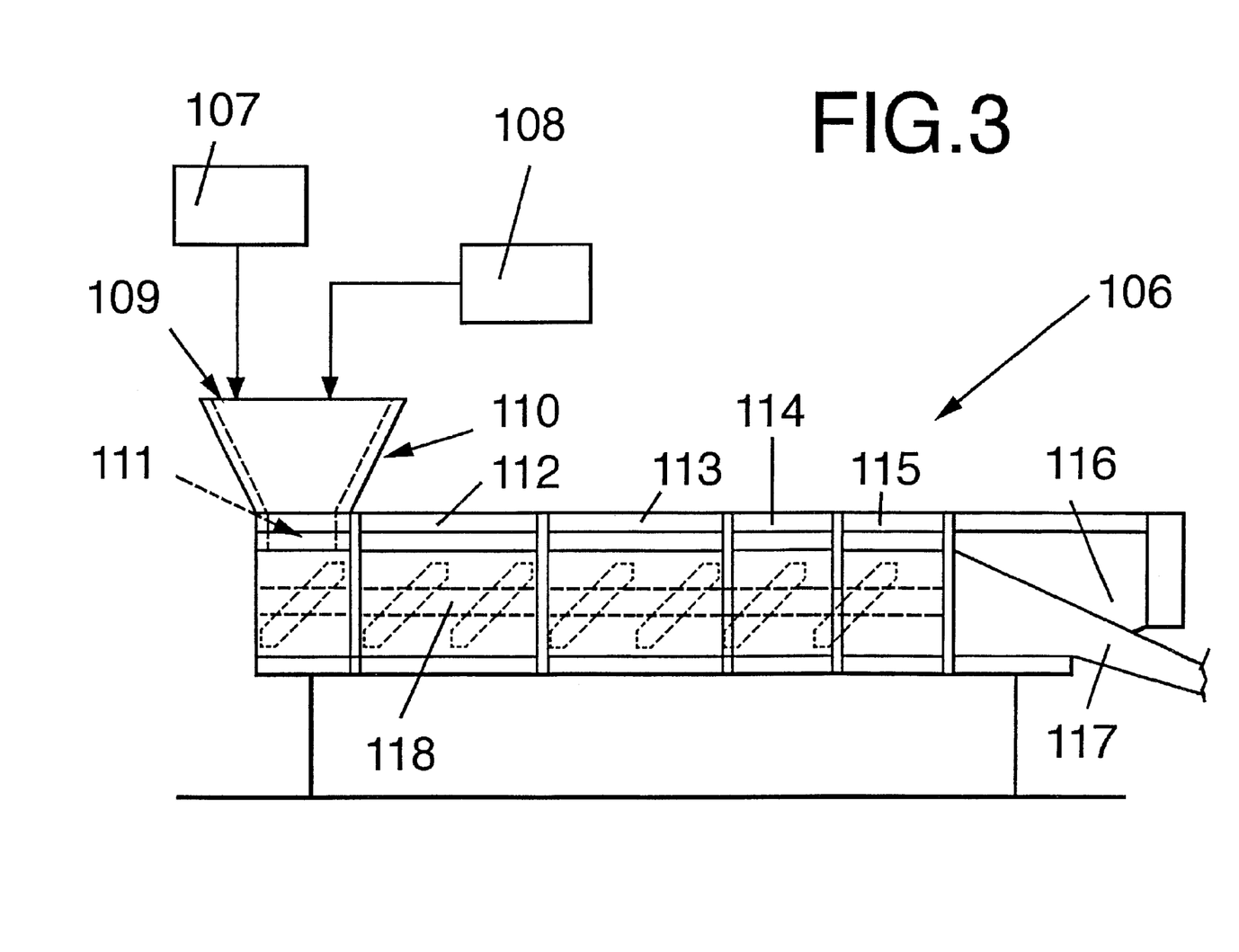
FIG. 3 is the detailed schematic flow diagram of the extrusion step of the process of our invention referring to the details of that part of the block flow diagram of FIG. 1 indicated by reference numerals 16, 17,18 and 19.

Thus, the plated olfactory sense effecting composition on silica from location 107 is admixed with molten maltose and mannitol from location 108 in FIG. 3 and enters the extruder at the extruder entrance zone 110 via entry opening 109, the extruder entry zone being indicated by reference numeral 111. The mixture of molten maltose and mannitol taken together with the plated olfactory sense effecting composition of matter on silica in the extruder is shown by reference numeral 118. The extrusion mixture passes through temperature control zones 112, 113, 114 and then finally 115 into the extruder output zone 116, the exiting tow being indicated by reference numeral 117 and the overall extrusion apparatus being indicated by reference numeral 106 in FIG. 3.

Figure 4:
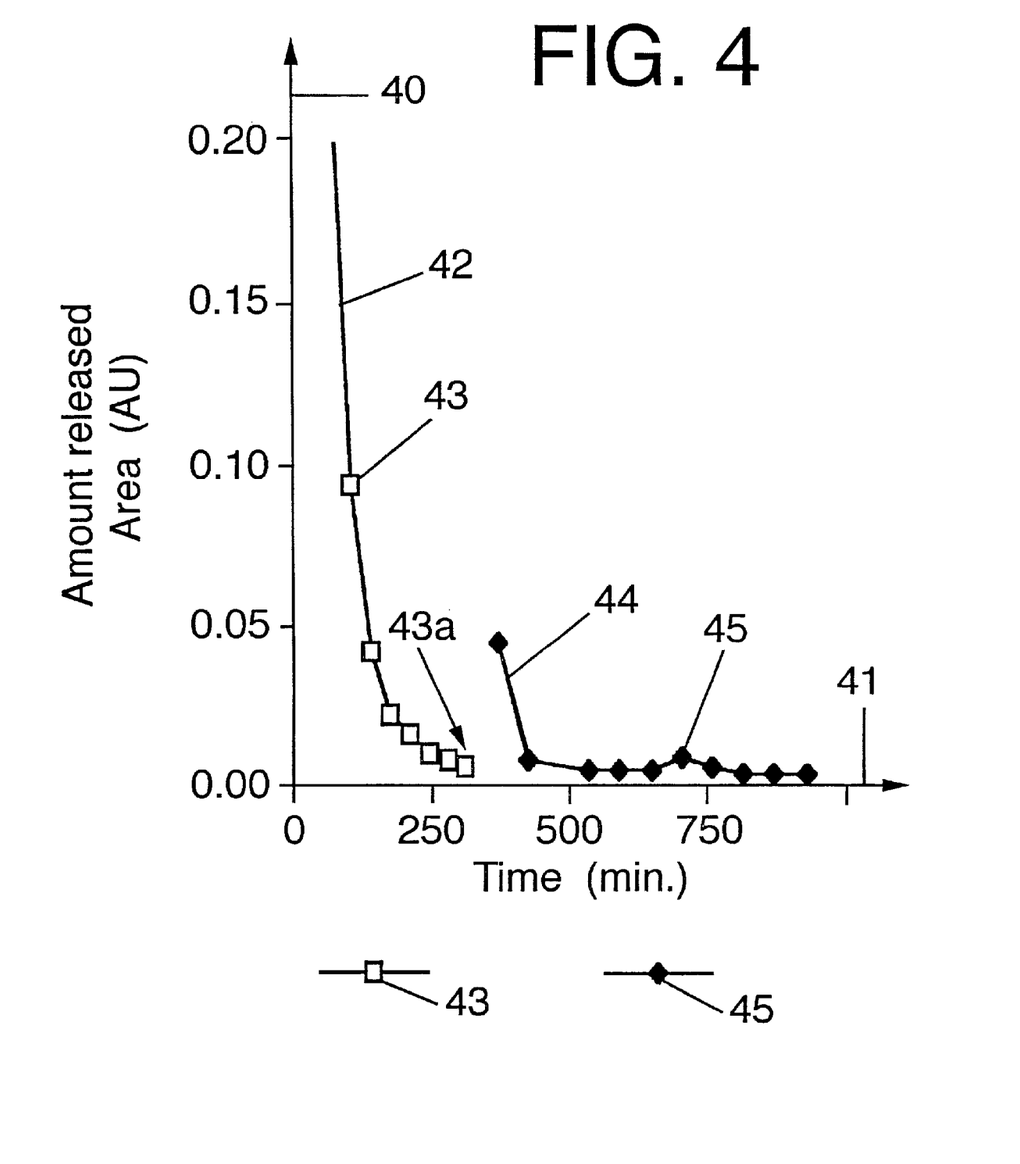
FIG. 4 is a graph showing the rate of fragrance composition release from a deodorant stick containing particles of our invention, with amount of fragrance composition released on the Y axis vs. time (minutes) on the X axis and showing a break in the curve where an initial burst of fragrance composition occurs when the particles are exposed to water.

Referring to the graph of FIG. 4, the Y axis shows amount released and is indicated by reference numeral 40, with the units being units of GC profile peak area. The X axis shows time in minutes. The graph is for particles of our invention wherein a 50:50 mixture of maltose and mannitol is extruded with 20% fragrance composition on hydrophobic silica particles. The graph is indicated by reference numeral 42, and the data points indicated by reference numeral 43 are for dry particles. Reference numeral 43a indicates that data point where water is introduced to the dry particles, wherein a "burst" of aroma occurs and the graph continues as indicated by reference numeral 44. The data points indicated by reference numeral 45 are for the wet particles.

Figure 5:
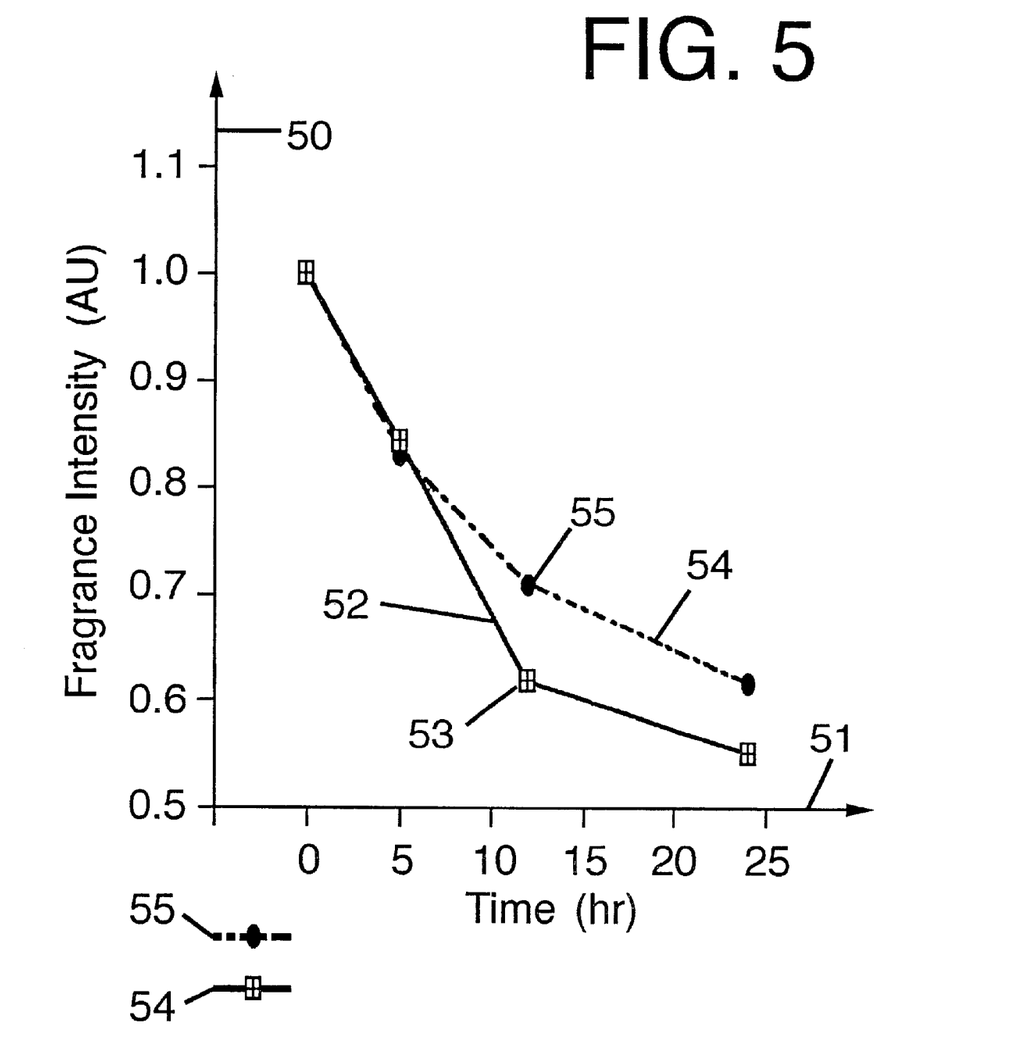
FIG. 5 is a graph showing fragrance composition intensity vs. time and showing the effect of encapsulation of fragrance composition (in the particles of our invention) on fragrance composition release when the particles of our invention are placed on the human epidermis (skin).

Referring to FIG. 5, FIG. 5 shows the graph for the effect of encapsulation into the particles of our invention on fragrance release on human epidermis (skin) wherein the particles are produced from a blend of 50:50 maltose:mannitol with 20% fragrance plated on hydrophobic silica. Fragrance intensity (in aroma units) is indicated on the Y axis by reference numeral 50 and time in hours is indicated on the X axis by reference numeral 51. The graph indicated by reference numeral 52 and the data points indicated by reference numeral 53 are for the control; that is, are for eight fragrance materials placed on skin. The graph indicated by reference numeral 54 and the data points indicated by reference numeral 55 are for the actual particularized fragrance of our invention. In general, this graph shows that the particles of our invention improve fragrance performance after a period of about 7 hours.

Figure 6:
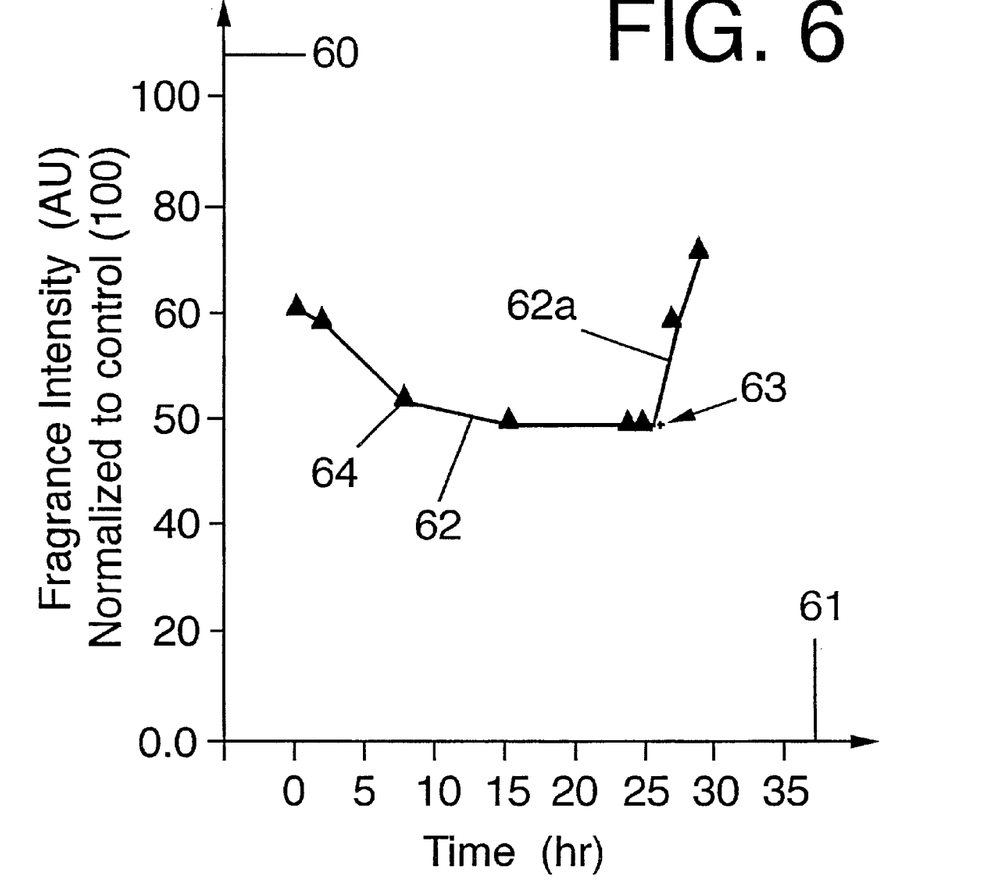
FIG. 6 is a graph showing fragrance composition intensity (normalized to a control) vs. time for the particles of our invention which are exposed to water after 26 hours.

FIG. 6 shows a graph for the sensory evaluation of fragrance composition release when the particles of our invention are placed in a deodorant stick, and the deodorant stick is used for application to human epidermis (skin). The X axis is indicated by reference numeral 61 and is for the variable of time (hours). The Y axis is indicated by reference numeral 60 and is for fragrance intensity normalized to a control. The graph is indicated by reference numeral 62 and the data points for the graph are indicated by reference numeral 64. 0.5 Ml of water is added to the skin containing the particles coated thereon at a time point of 26 hours, shown at reference numeral 63 on the graph. That portion of the graph showing aroma burst as a result of water application is indicated by reference numeral 62a.

Figure 7:
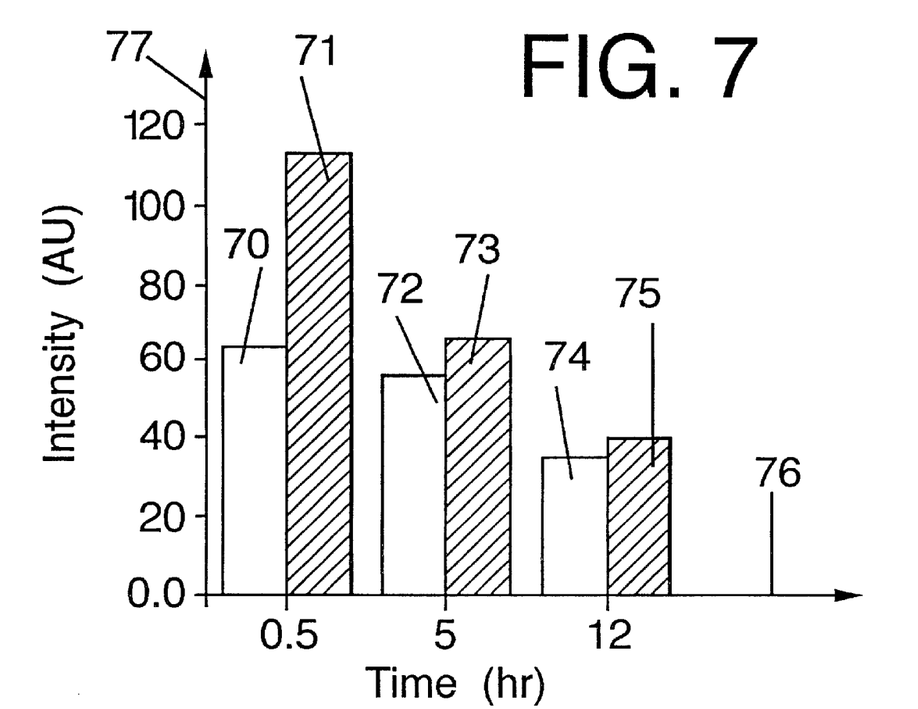
FIG. 7 is a graph of intensity vs. time showing a comparison of limonene encapsulated in the particles of our invention vs. neat limonene when both materials are placed on the human epidermis (skin) with the placement of the materials onto the skin using a deodorant stick.

Referring to FIG. 7, FIG. 7 is a graph showing intensity of limonene encapsulated in the particles of our invention compared to neat limonene when placed on human epidermis (skin) using a deodorant stick as prepared in Example II, infra. Intensity (in aroma units) is shown on the Y axis by reference numeral 77 and time in hours is shown on the X axis using reference numeral 76. The bar graphs (comparative) are shown for 0.5 hours, for 5 hours and for 12 hours. Thus, the bar graph indicated by reference numeral 70 is for the intensity of neat limonene at a period of 0.5 hours. The bar graph indicated by reference numeral 71 is for encapsulated limonene at 0.5 hours. The bar graph indicated by reference numeral 72 is for neat limonene at 5 hours. The bar graph indicated by reference numeral 73 is for encapsulated limonene at 5 hours. The bar graph indicated by reference numeral 74 is for neat limonene at 12 hours. The bar graph indicated by reference numeral 75 is for encapsulated limonene at 12 hours.

This invention will now be described by reference to the following specific examples. These examples are intended to be illustrative, and the invention is only limited according to the subject matter of the claims. All parts and percentages are by weight unless otherwise indicated.

EXAMPLE I

The following fragrance is prepared by admixing the following ingredients:

| Ingredients | Parts by Weight |
| --- | --- |
| GALAXOLIDE ® | 41.4 |
| the formic acid ester of α-hydroxy ethyl-3,3-dimethyl cyclohexane | 18.4 |
| p-t-butylcyclohexyl acetate | 18.4 |
| peach aldehyde | 9.2 |
| prenyl acetate | 3.2 |

| Ingredients | Parts by Weight |
| --- | --- |
| bicyclopentadiene propionate | 3.2 |
| n-amyl butyrate | 4.3 |
| ethyl isovalerate | 4.2 |
| ethyl tiglate | 4.4 |
| l-carvone | 8.2 |
| ethyl methyl phenyl glycidate | 3.2 |
| allylyclohexyl propionate | 4.1 |
| ethyl cinnimate | 3.2 |
| isocyclocitral | 12.3 |

The resulting fragrance has an excellent musk aroma with citrus topnotes and woody undertones.

EXAMPLE II PREPARATION OF A DEODORANT STICK

In accordance with the process shown in FIG. 1 the fragrance of Example I, supra, is plated onto hydrophobic silica (SIPERNAT® D-17 manufactured by the Degussa Chemical Corporation) according to the diagram as set forth in FIG. 2, described in detail, supra. The maltose:mannitol blend melt is then combined with the fragrance-plated silica and placed into a Werner & Phleiderer twin screw extruder as described in the detailed description of FIG. 3, supra.

The Wemer & Phleiderer extruder is then operated at a feed rate of 18.14 kg per hour with the barrel indicated by reference numeral 111 operated at 96° C.; the barrel indicated by reference numeral 112 operated at 104° C.; the barrel indicated by reference numeral 113 operated at 91° C.; the barrel indicated by reference numeral 114 operated at 75° C.; the barrel indicated by reference numeral 115 operated at 74° C.; and the exit barrel and the exit zone barrel operated at 140° C. The plating apparatus of FIG. 2 is a NIRO AEROMATIC® fluidized bed apparatus. The tow exiting from the extruder is quickly chilled in a liquid quenching medium (water at 5° C.) and pelletized. The resulting pellets containing fragrance are then cryogenically ground using liquid nitrogen to achieve an encapsulated fragrance having an average particle size of 30 microns.

A wax-type deodorant stick formulation having the following formulation is prepared by mixing:

| Ingredients | Parts by Weight |
| --- | --- |
| ARISTOWAX ® 165 (registered trademark of Witco Chemical Corporation for paraffin wax) | 14.0 |
| ozocerite wax 170-D (hydrocarbon wax) | 8.0 |
| white petrolatum | 13.0 |
| ACETULAN ® (acetylated lanolin oil manufactured by Amerchol Chemical Company) | 2.8 |
| di-isopropyl adipate | 6.0 |
| mineral oil | 52.1 |
| propyl paraben | 0.1 |

The resulting composition is heated to 75° C. until melted. With stirring, 4.0 parts by weight of the encapsulated reference as prepared in this Example, supra, is added to the wax deodorant stick formulation while maintaining the temperature at 75° C. The resulting mixture is stiffed in order to ensure a uniform suspension of the encapsulated fragrance particles in the deodorant stick. The resulting suspension is then poured into stick molds, thereby formulating deodorant sticks containing encapsulated fragrance suspended therein, each stick being cylindrical and having a length of 3 inches and a diameter of 1 inch.

A similar product is produced without the encapsulated fragrance. A panel test is conducted on 30 independent panelists to determine which product produced the strongest fragrance after 8 hours. Of the 30 panel members, 25 panelists (83.3%) perceived the fragrance produced from the encapsulated fragrance to be three times as strong. Three panelists think that the product without the encapsulated fragrance is somewhat stronger, and two of the panelists think that neither fragrance is stronger than the other.

EXAMPLE III PREPARATION OF ANTIPERSPIRANT/DEODORANT

(i) Preparation of Antiperspirant/Deodorant Base

66 Grams of propylene glycol are combined with 27 grams of distilled water 7 Grams of sodium stearate are slowly added with mixing and heated to 80° C. until dissolved. The composition is mixed and poured into ingredient stick molds. The following antiperspirant/deodorant samples are prepared at 1.25 effective fragrance concentration in the antiperspirant/deodorant base;

(ii) Preparation of Antiperspirant/Deodorant with Neat/Encapsulated Fragrance An encapsulated fragrance was prepared in the same manner as is set forth in Example II, supra. 24.34 Grams of the above antiperspirant/deodorant base is melted on a hotplate. The base is admixed with the encapsulated fragrance mixture. The resulting product is poured into a deodorant stick mold to produce a 25 gram antiperspirant/deodorant stick;

(iii) Preparation of Antiperspirant/Deodorant with Neat Fragrance

A neat fragrance sample is prepared as follows:

24.688 Grams of the base of (i) was melted on a hotplate and slowly added to 0.312 grams of fragrance of Example I. The product is poured into a deodorant stick mold to produce a 25 gram antiperspirant/deodorant stick.

The resulting deodorant/antiperspirant sticks are unanimously preferred by a panel of 30 panelists. Each of the panelists indicated that the deodorant/antiperspirant stick containing the encapsulated fragrance lasts twice as long as the deodorant stick containing the neat fragrance of Example I. Furthermore, each of the panelists indicated that when, after 5 hours, the area treated with the antiperspirant/deodorant stick containing the encapsulated fragrance is washed, a burst of aroma occurs, which is aesthetically pleasing.

EXAMPLE IV TOOTHPASTE COMPOSITION

The following toothpaste composition is prepared:

| Ingredients | Parts by Weight |
| --- | --- |
| calcium phosphate | 500 |
| carboxymethyl cellulose | 10 |
| sodium lauryl sulfate | 20 |
| glycerol | 250 |
| saccharin | 2 |
| toothpaste flavor X-9135 (flavor made by Takasago International Corporation) | 8 |
| encapsulated menthol prepared according to the process of Example II (as described in the description of FIG. 1 in the Detailed Description of the Drawings) | 4 |
| water | q.s. to 1,000 |

The components described above were mixed by a blender according to the foregoing formulation to provide a toothpaste. When the product was used as a toothpaste, an excellent, refreshing effect was obtained with the flavor lasting for a period of 3 hours after use.

EXAMPLE V CHEWING GUM

The following chewing gum formulation was prepared:

| Ingredients | Parts by Weight |
| --- | --- |
| gum base | 230 |
| powdered sugar | 480 |
| glucose | 160 |
| starch syrup | 118 |
| plasticizer | 1 |
| cola flavor E-7002 (flavor made by Takasago International Corporation) | 10 |
| encapsulated menthol encapsulated according to the process of Example II and described in the Detailed Description of the Drawings, describing the process of FIG. 1 | 8 |

The components described above were kneaded by a kneader according to the foregoing formulation to provide a chewing gum. The mint flavor of the chewing gum lasted for a period of 1 hour from the time that the chewing commenced.

What is claimed is:

1. A particulate composition consisting essentially of solid particles which (i) controllably release one or more olfactory sense effecting composition of matter therefrom into the environment surrounding said particles and (ii) provide a burst release of one or more olfactory sense effecting compositions of matter when contacted with water, each of which particle has an effective diameter in the range of from about 10 microns up to about 50 microns, each of which particle is an 80–140° C. -extruded, cryogenically-ground matrix of at least one olfactory sense effecting composition of matter-bearing silica particle containing from 40–70% of one or more olfactory sense effecting compositions, intimately admixed with a saccharide composition consisting essentially of a mixture of maltose and mannitol, with the weight ratio of maltose: mannitol being in the range of from about 10 parts mannitol:60 parts maltose down to 60 parts mannitol:10 parts maltose.

2. The particulate composition of claim 1, wherein the olfactory sense effecting composition of matter is a fragrance composition.

3. The particulate composition of claim 1 wherein the olfactory sense effecting composition of matter is a fragrance composition component.

4. The particulate composition of claim 1 wherein the olfactory sense effecting composition of matter is a flavor composition.

5. The particulate composition of claim 1 wherein the olfactory sense effecting composition is a flavor composition component.

6. A flavored chewing gum comprising a chewing gum base and intimately admixed therewith a flavor composition of claim 4.

7. A toothpaste composition comprising a toothpaste base and intimately admixed therewith an aroma or taste augmenting, enhancing or imparting composition defined according to claim 4.

* * * * *